United States Patent [19]
Karakasoglu et al.

[11] Patent Number: 5,797,852
[45] Date of Patent: Aug. 25, 1998

[54] SLEEP APNEA SCREENING AND/OR DETECTING APPARATUS AND METHOD

[75] Inventors: Ahmet Karakasoglu, Mountain View; Chin N. Hung, Santa Clara; Anthony F. Matouk, Los Altos; Lawrence C. Grotte, San Carlos, all of Calif.

[73] Assignee: Local Silence, Inc., San Jose, Calif.

[21] Appl. No.: 472,441

[22] Filed: Jun. 7, 1995

Related U.S. Application Data

[63] Continuation-in-part of Ser. No. 206,464, Mar. 4, 1994, abandoned, and Ser. No. 206,462, Mar. 4, 1994, which is a continuation-in-part of Ser. No. 206,464, Mar. 4, 1994, which is a continuation-in-part of Ser. No. 38,336, Feb. 4, 1993, abandoned.

[51] Int. Cl.$^6$ .................................................. A61B 5/08
[52] U.S. Cl. .................................................. 600/529
[58] Field of Search .................... 128/716, 633, 128/670–671, 706, 715, 721, 719

[56] References Cited

U.S. PATENT DOCUMENTS 4,129,125 12/1978 Lester et al. ............... 128/715 X
4,862,144 8/1989 Tao .............................. 128/721 X
4,956,867 9/1990 Zurek et al. .
5,385,144 1/1995 Yamanishi et al. ........... 128/633 X

*Primary Examiner*—John P. Lacyk
*Assistant Examiner*—Ryan Carter
*Attorney, Agent, or Firm*—Flehr Hohbach Test Albritton & Herbert LLP

[57] ABSTRACT

Sleep apnea screening and/or detection apparatus for use by a patient breathing through the nose and/or mouth and producing an air flow into and out of the lungs of the patient and creating audible sounds. It is comprised of a first microphone positioned in the vicinity of the patient's nose and mouth and out of contact therewith to pick up audible sounds created by breathing of the patient and providing a first electrical analog signal. A second microphone is provided which is positioned near the patient for picking up ambient noise in the vicinity of the patient and providing a second electrical analog signal, an active noise controller is provided for combining the first and second electrical analog signals to provide a third electrical signal for generating a fourth electrical signal providing a waveform which is closely correlated with the air flow of the patient. A classifier is provided for classifying the electrical waveform provided by the fourth electrical signal to determine when a disordered breathing event has occurred.

18 Claims, 7 Drawing Sheets

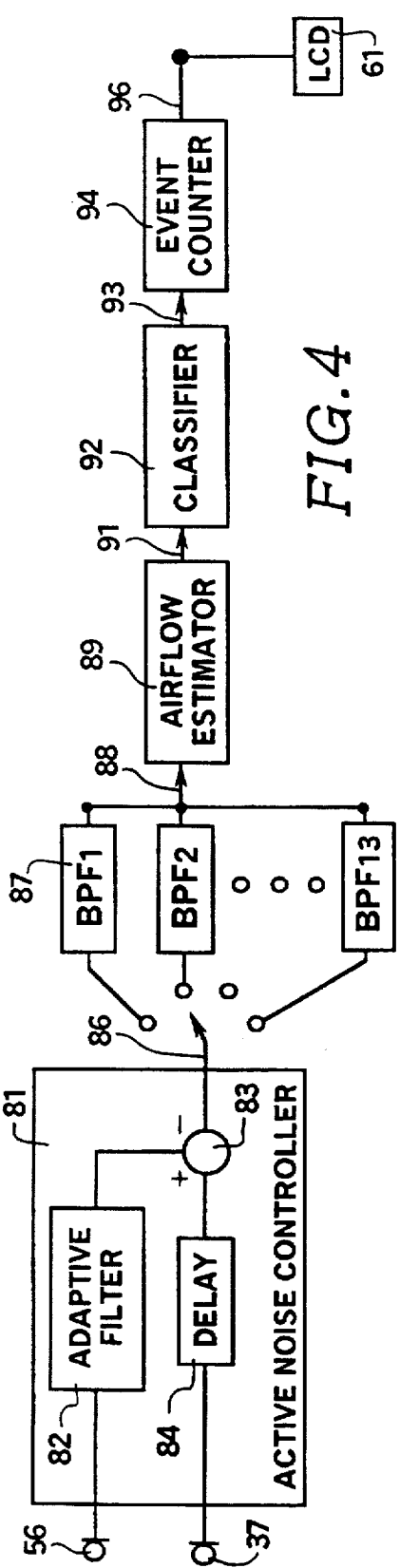
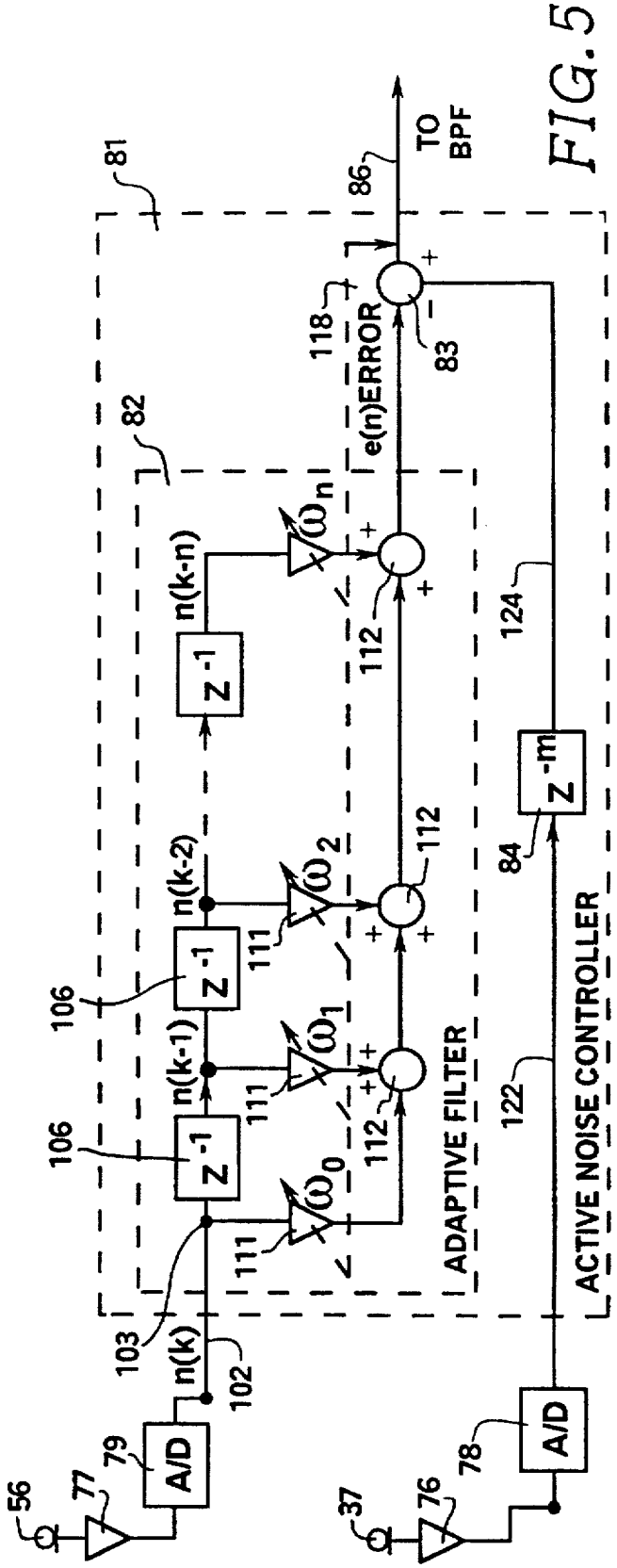

1

SLEEP APNEA SCREENING AND/OR DETECTING APPARATUS AND METHOD

This application is a continuation-in-part of application Ser. No. 08/206,464 filed on Mar. 4, 1994, now abandoned which is a continuation in part of application Ser. No. 08/038,336 filed on Feb. 4, 1993, now abandoned and also a continuation-in-part of application Ser. No. 08/206,462 filed on Mar. 4, 1994 which is a continuation-in-part of application Ser. No. 08/206,464, now abandoned filed on Mar. 4, 1994 which is a continuation-in-part of application Ser. No. 08/038,336 filed on Feb. 4, 1993 now abandoned.

This invention relates to a sleep apnea screening and/or detection apparatus method and more particularly to such an apparatus and method of which is designed for early recognition on an out-patient basis for use in the home.

Portable sleep apnea recorders designed for early recognition on an out-patient basis have heretofore been available. However, such recorders have required the use of multiple channels of information for example as many as four to sixteen channels requiring the affixing of various sensors to the patient prior to the patient going to sleep. Such sensors have included, for example, thermocouples disposed in the nasal area to determine respiratory air flow, a pulse oximeter attached to a finger for purposes of capturing oxygen saturation and pulse rate sensors attached to one or more limbs to determine limb movement during sleep and body position sensors to determine whether the patient is sleeping on his side or is in a supine position. In such multi-channel devices such information is typically recorded on a tape recorder in the device. The recorded information on the tape is then taken to the doctor's office where it is downloaded into a computer for analysis by the doctor or technician. Such recorders have a number of disadvantages. Since a number of sensors are required, they must be properly attached in order to obtain the desired data. The multiplicity of sensors required may interfere with the patient's sleep. Use of such recorders is also undesirable because it requires post-processing in the doctor's office and requires the use of additional expensive equipment. Such recorder devices in addition are relatively expensive. There is therefore a need for a new and improved apparatus and method for the screening and/or detection of sleep apnea.

SUMMARY OF THE INVENTION

In general, it is the object of the present invention to provide an aural sleep apnea screening and/or detection apparatus and method which only requires the use of a single channel of data.

Another object of the invention is to provide an apparatus and method of the above character which gives real time information and which does not require post-processing.

Another object of the invention is to provide an apparatus and method of the above character which identifies the specific apnea events as they occur to provide a direct and real time apnea indicator.

Another object of the invention is to provide an apparatus and method of the above character which is totally non-invasive and non-contacting with respect to the patient.

Another object of the invention is to provide an apparatus and method of the above character which has continuous monitoring capabilities.

Another object of the invention is to provide an apparatus and method of the above character which can be utilized in post-operative situations.

Another object of the invention is to provide an apparatus and method of the above character which is portable, small in size and of a low cost so that it is possible if the patient desires to purchase the same.

Another object of the invention is to provide an apparatus and method of the above character which is a portable, ambulatory risk assessment device with continuous monitoring capabilities which is capable of handling data from a single channel with a high degree of accuracy.

Another object of the invention is to provide an apparatus and method of the above character which permits patients with sleep related sleeping disorders to be pre-selected before they are subjected to expensive and time consuming sleep laboratory investigations.

Another object of the invention is to provide an apparatus and method of the above character which makes possible patient monitoring on a continuous basis during therapy, for treatment evaluation and after surgery.

Additional objects and features of the invention will appear from the following description in which the prepared embodiments are set forth in detail with conjunction with the accompanying drawings.

BRIEF DESCRIPTION OF THE DRAWINGS

FIG. 4 is an electrical block diagram of the apparatus shown in FIG. 1.

FIG. 5 is a detailed block diagram of the active noise control as shown in FIG. 4.

DETAILED DESCRIPTION

In general the sleep apnea screening and/or detection apparatus of the present invention is for use by a patient breathing through the nose and/or mouth and producing an air flow into and out of the lungs of the patient and creating audible sounds. It is comprised of a first microphone positioned in the vicinity of the patient's nose and mouth and out of contact with the patient to pick up audible sounds created by breathing of the patient and providing a first electrical signal. A second microphone is positioned near the patient for picking up ambient noise in the vicinity of the patient and provides a second electrical signal. Means is provided for combining the first and second electrical signals to provide a third electrical signal. Means is provided operating on the third electrical signal for generating a fourth electrical signal providing an electrical waveform which is closely correlated with the patient's air flow and respiration. Means is provided for classifying the electrical waveform provided by the fourth electrical signal to determine when a disordered breathing event has occurred.

Figure 1:
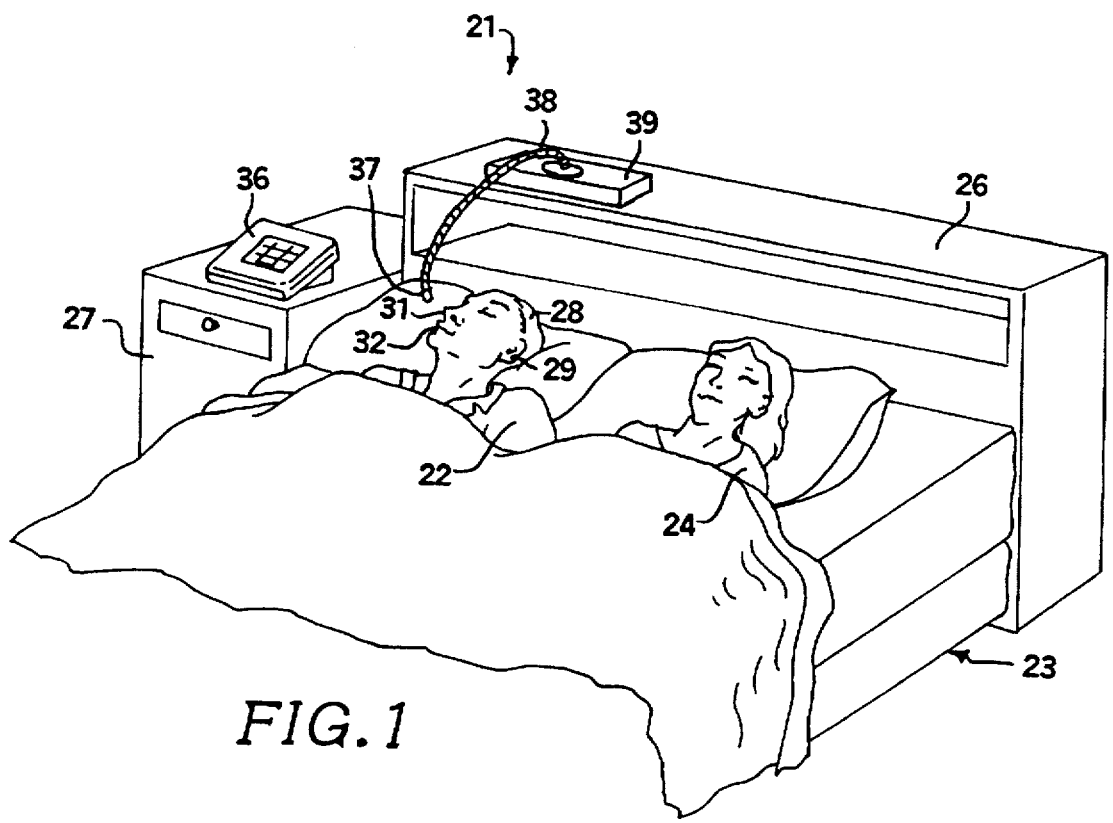
FIG. 1 is an isometric view showing sleep apnea screening and/or detection apparatus incorporating the present invention being utilized by a patient lying in a bed.

More in particular the sleep apnea screening and/or detection apparatus 21 as shown in FIG. 1 is a portable type apparatus or device which is adapted to be utilized in the patient's home for overnight out-patient sleep studies. A patient 22 is shown lying on a bed 23 with a sleep mate 24. The bed 23 is provided with a headboard 26 and a nightstand 27 of a conventional type. The patient as shown has a head 28 having ears 29 on opposite sides of the head 28 and receiving audible sounds and a nose 31 and a mouth 32 on the front of the head 28 through which breathing occurs for supplying air into the lungs during inhalation and air from the lungs during exhalation. It is this breathing by the patient which creates the breathing sounds to be detected and analyzed in accordance with the present invention.

The apparatus 21 includes a control console 36 typically mounted on the nightstand adjacent the patient 22 which is adapted to be connected to a conventional electrical outlet (not shown). The control console 36 is connected to a first microphone 37 which is carried by an adjustable goose neck 38 affixed to a base 39 resting on the headboard 26 as shown in FIG. 1. The microphone 37 is positioned so that it is in relatively close proximity to but not in contact with the nose 31 and the mouth 32 of the patient 22 which is undergoing the overnight sleep study. The power cord is provided with a conventional AC/DC adapter (not shown) to supply the desired DC power to the circuitry provided in the control console 36.

The control console 36 includes a case 41 consisting of a base 42 and a cover 43. The base 42 is provided with a recessed lower portion 42a which inclines forwardly and downwardly so that the cover 43 is inclined in a forwardly and downwardly extending direction shown in FIG. 2. A printed circuit board 46 carrying electronic components of the type hereinafter described is mounted within the case 41. A power-in plug 47 is mounted in the lower portion 42a of the base 42 on the rear side thereof and underlies the printed circuit board 46. A battery 48 of a suitable type, as for example, a twelve-volt rechargeable battery string is mounted in the base 42 underlying the printed circuit board 46 and is connected in a conventional manner to the power-in plug 47 so that it remains charged and provides power in the event of a power failure. A microphone plug 51 for receiving the electrical connectors (not shown) from the microphone 37 is mounted in the base portion 42a. A power on/off switch 52 is mounted on the rear side of the base 42 and is connected to the power in plug 47.

Figure 3:
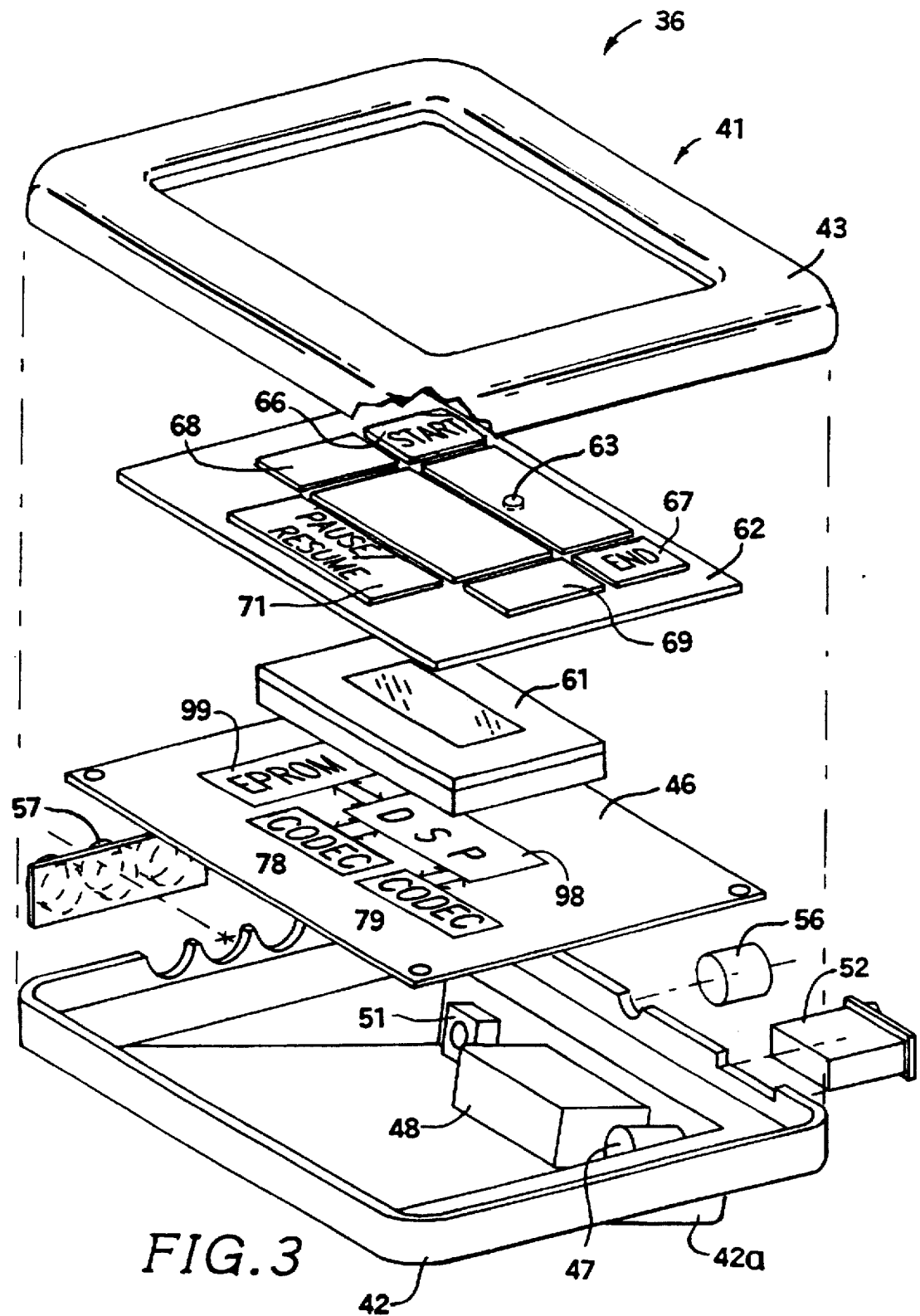
FIG. 3 is an exploded view of the console shown in FIG. 2.

An ambient noise microphone 56 which is utilized for a purpose hereinafter described is mounted on the rear side of the base 42 generally equidistant from the sides thereof and is exposed to ambient noise on the rear side of the case 41. A plurality of time setting switches 57 are mounted in one side of the base 42 shown in FIG. 3.

A backlit liquid crystal display 61 is mounted within the case 42 and underlies a membrane switch control panel 62. A power-on light 63 is mounted on the control panel 62. The control panel includes a start switch 66, an end switch 67, scrolling switches 68 and 69 and a pause and resume switch 71.

Figure 2:
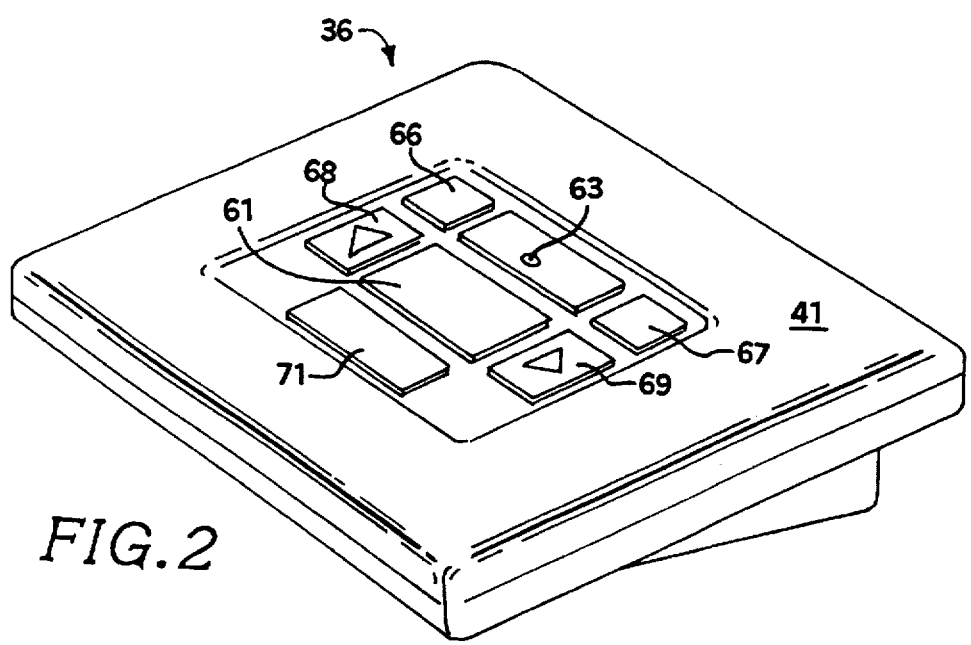
FIG. 2 is an isometric view of the control console utilized in the apparatus shown in FIG. 1.

The case 41 when assembled has the attractive appearance as shown in FIG. 2 and is adapted to readily fit on the surface of the nightstand 27.

The block diagram of the circuity which is carried by the printed circuit board 46 is shown in the block diagram FIG. 4. As shown therein, the breathing signal microphone 37 and the ambient noise microphone 56 which provide first and second analog signals are connected through amplifiers 76 and 77 and analog-to-digital (A/D) converters 78 and 79 to supply digital signals into an active noise controller 81. The digital signal from the ambient noise microphone 56 is supplied through an adaptive filter 82 to an adder or summer 83. The digital signal from the breathing microphone 37 is supplied through a delay 84 and connected into the adder or summer 83 to arrive in unison with the ambient noise digital signal so that the ambient noise digital signal is subtracted to supply a cleaned combined digital output signal which can be considered as a third electrical signal 86 to band-pass filter network 87. The band-pass filter network 87 is comprised of a plurality of sections identified as BPF 1 through BPF 13. The output 88 from the band-pass filter network 87 in the form of a further cleaned third electrical signal is supplied to an air flow estimator 89. The output 91 of the air flow estimator 89 is supplied to a classifier 92. The output 93 from a classifier 92 is supplied to an event counter 94. The output 96 from the event counter 94 is supplied to various output devices as for example the backlit liquid crystal display 61 shown in FIG. 1.

The electrical functions described in conjunction with FIG. 4 and in accordance with the present invention are carried out principally by the use of electronic components mounted on the printed circuit board 46 (see FIG. 3) and include a 60 mHz version of the Motorola 56002 digital signal processor DSP 98 which is supplied with the digital signals from the A/D converters 78 and 79 which can be of a switch type such as a CODEC CS 4215 supplied by Crystal Semiconductor. An EPROM 99 is mounted on the PC board 46 and provides the desired memory for the DSP 98. A suitable algorithm incorporating the electrical functions shown in FIG. 4 and described hereinafter in additional detail can be readily implemented by one skilled in the art into appropriate software and downloaded onto the Motorola 56002 digital signal processor which also can be called as Motorola DSP 56002 chip.

A more detailed block diagram representative of the software of the active noise controller 81 is shown in FIG. 5. As shown therein the electrical analog signal from the ambient noise microphone 56 is supplied through the amplifier 77 and A/D converter 79. The amplified noise signal is supplied on a line 102 to the adaptive filter 82. The signal line 102 is connected to a junction 103 in the adaptive filter. The junction 103 is connected to a plurality of serially connected filter units 106 that carry the designation $Z^{-1}$ to provide successive sampling. Each represents a sampling period delay or in other words a discrete time filter tap to provide a tapped delay version of the ambient noise electrical signal supplied by the microphone 56. Thus each delay unit 106 provides an output which is a delayed sequence of the ambient noise signal. The length of the adaptive filter 82, in other words the number of delay units 106 in the adaptive filter 82, is determined by what extent it is desired to clean the noise component from the signal picked up by the electrical signal supplied by the signal microphone 37. Thus a number of filter units 106 are provided as shown in FIG.

5 indicated by "n" with "k" representing the sampling. Thus the first delay unit 106 in the adaptive filter 82 provides a delay of $n^{(k-1)}$ with the last delay unit 106 providing a delay of $n^{(k-n)}$. The delayed sequential output signal provided by each delay unit 106 is weighted to provide means for modeling the acoustic difference between the two acoustical signals picked up by the noise microphone 56 and signal microphone 37. Thus there are provided a plurality of weighting units 111. As shown, a weighting unit 111 is provided for each of the delay units 106 and is connected to the output of the delay unit 106 as shown in FIG. 5. The weighting units 111 are represented as adjustable amplifiers and carry the designations of $\omega_0$, $\omega_1$, $\omega_2$ with the last weighting unit 111 being identified as $\omega_n$. The outputs of the weighting units 111 are connected into serially connected adders or summers 112 which are connected into an adder or summer 83 connected to the output 86.

The electrical signal from the signal microphone 37 is supplied through the amplifier 76 and the A/D converter 78 through a conductor line 122 to the delay network 84 carrying the designation $Z^{-m}$ which provides an output on line 124 also connected to the adder or summer 83 to provide an output signal on line 86 which has been cleaned of its noise component. The output on line 86 is monitored by a feedback leg 118 coupled to the adjustable weighting units 111. By appropriate weighting, the error term e(n) is minimized. These gains of the weighting units 111 are established in the algorithm used in the Motorola DSP chip by a trial and error method analogy. Initially all of the gains are set to zero. The weighting values of the gains are updated during successive sampling until the error term e(n) is appearing on the output line 86 has been minimized. The weighting values are derivative values and are ascertained by the gradient descent search techniques. Since the active noise controller 81 includes an adaptive controller, all weighting values are continuously updated. The delay element in network 84 provides an artificial delay to make the active noise controller 81 act as a causal system. The delay network 84 provides an artificial delay making the system shown in FIG. 4 work in a real time environment often called causality to make it unnecessary to forecast future values.

The model employed to develop the acoustical transfer function for the room in which the patient 22 is sleeping and interconnecting the two microphones 56 and 37 is represented by a transversal filter consisting of a set of delay-line elements each of which is represented by one sampling period of delay and a corresponding set of adjustable coefficients as hereinbefore explained.

At the sampling time instant k, the available signal collected by the noise microphone 56 consists of a set of samples $$u(k-1), u(k-2) \ldots u(k-n)$$

Multiplying by a corresponding set of adjustable tap weights $$\omega_0, \omega_1, \omega_2, \ldots, \omega_n$$

to produce an output signal y(n). The signal collected by the breathing/snoring microphone 37 can be designated as d(n). The filter output y(n) is compared with the d(n) to produce an estimation error e(n) which is used by the adaptive algorithm to control the corrections applied by the individual tap weights. The process is continued until the noise estimation error e(n) becomes sufficiently small. In order to keep the estimation algorithm causal, during its operation, an internal time delay (d) is added to the reference ambient noise signal from the microphone 56. The time duration of d is selected based on the sampling rate and the distance between the two microphones.

Thus it can be seen by providing the active noise controller 81, it is possible to clean up the breathing signal which is received from the microphone 37 to subtract out room noise and other ambient noise to provide a clean signal that provides the information which can be utilized for screening and/or detection as hereinafter described.

Improved performance can be obtained from the active noise controller by increasing the sampling frequency. However, increasing the sampling frequency increases the computational power required. The sampling frequency is dependent on the physical distance between the two microphones 56 and 37 with the ambient noise microphone 56 typically being located in the control console 36 on the nightstand and the adjustable microphone 37 extending over the head of the patient 22. Typically the microphone is spaced from the head of the patient by approximately one foot being out of contact with the patient so that it is totally a non-contacting and with the spacing between the two microphones 37 and 56 being from one to fifteen feet and preferably two to five feet. By way of example utilizing a sampling frequency of 5.6 kilohertz it may be desirable to provide an active noise controller having approximately 200 taps and 50 delay units at an operational sampling period of 0.178 milliseconds. For sound to travel one foot requires approximately 0.83 milliseconds which can be represented by five taps and for sound to travel fifteen feet can be represented by approximately 150 taps. Considering the delay which is provided by the delay unit 84 which could represent approximately 50 taps, these 50 taps are added to the hereinbefore described number of 5 or 150 taps to provide a range of taps from 50 to 200. In order to avoid varying the range for each application of the apparatus in the present invention, it has been found desirable to provide 200 taps which are available at all times, so that it can be assured that a filter length can be provided which meets all normal requirements.

Nyquist sampling criteria have been used in the algorithm to ensure that the signals received from the microphone 37 and 56 are sampled by considering the highest frequency components in the signals. In accordance with the present invention breathing, snoring and other breathing noises are being sampled. Since these have frequency spectrum components which typically have a highest frequency in the 2 kHz range, a sampling rate of 4 kHz and above should be sufficient for applications of the present invention. The artificial delay inserted by the delay network 84 determined by the length of the adaptive filter 82 and by the distance between the two microphones 56 and 37. The Motorola DSP chip hereinbefore described has the capability of readily handling such sampling rates and delays while still permitting the chip to be utilized for other functions typically required in the system which they are used.

From the foregoing it can be seen that the active noise controller 81 receives from the microphone 37 the desired respiratory (breathing/snoring) sound signal of interest buried in the ambient noise. The ambient noise microphone 56 supplies the same ambient noise substantiated devoid of the breathing/snoring sounds of the patient 22. The two microphones 56 and 37 are positioned to confirm that (a) the signal and noise at the output of the microphones 56 and 37 are uncorrelated and (b) the noise at the output of the noise microphone is correlated with the noise component in the output of the signal microphone 37.

In summary it can be stated that the active noise controller 81 contains an adaptive filter which uses the output from the ambient noise microphone 56 as a reference signal which is in turn subtracted from the output from the signal microphone 37. The output from the ambient noise microphone 56 is utilized to adjust the tap weights in the adaptive filter 82. The adaptive filter 82 minimizes the mean-square value of the overall output causing it to be the best estimate of the desired signal in the minimum-mean-square sense.

As hereinbefore explained, the cleaned-up electrical signal from the microphone 37 is supplied on the line 86 to the band-pass filter network 87 which is comprised of a plurality of individually selectable band-pass filters 131 identified as BPF1 to BPF13 with each filter having a certain band-pass for example the 100 Hz band-pass extending over the spectrum of interest as for example the spectrum of sound breathing or snoring sounds of interest which as hereinbefore explained typically varies from 200 Hz to 1500 Hz so that 13 of such band-pass filters 131 can cover the spectrum of interest. A selection algorithm is utilized which sends the signal received on the line 86 through each of the 13 filters 131 and then looks at the output of each to ascertain which of the filters provides a maximum signal output to noise. This maximum output from this filter is selected to achieve an increased signal-to-noise ratio to further enhance the quality of the signal to be analyzed in connection with apnea screening and/or detection as hereinafter described.

Figure 6:
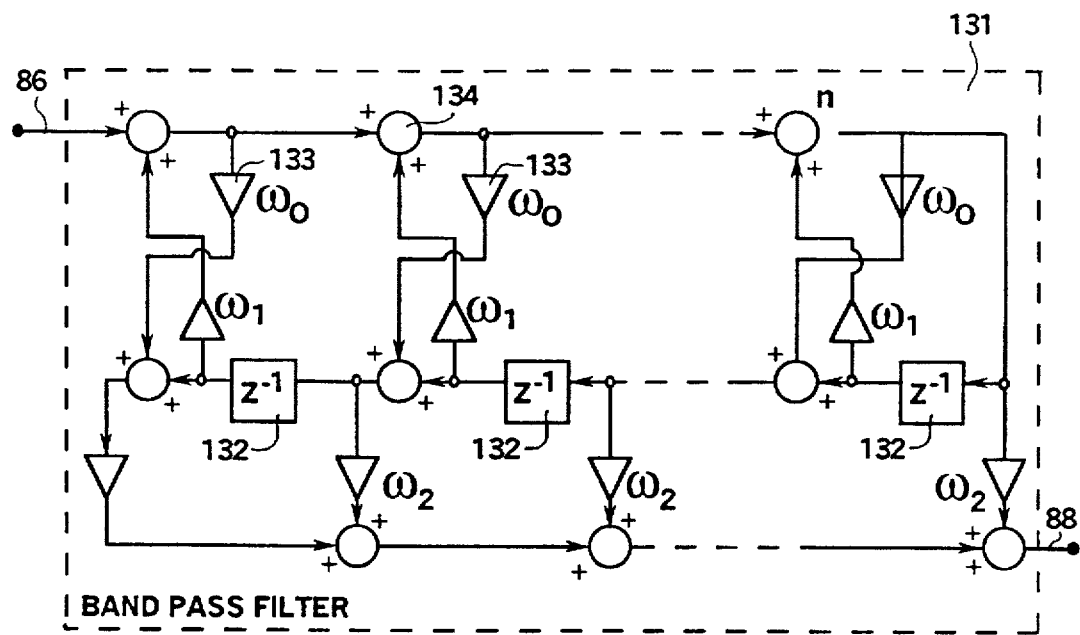
FIG. 6 is a more detailed block diagram of the band-pass filter shown in FIG. 4.

A typical band-pass filter which can be utilized in the present invention is shown in FIG. 6 and is merely being representative of one of the 13 band-pass filters 131. For example it can be a 200 Hz or 300 Hz fourth order Butterworth-type band-pass filter network having a flat response in the pass band and being monotonic overall. The filters are of the auto regressive-moving average (ARMA) type having both poles and zeros. The network 131 is interconnected as shown through a plurality of amplifiers 133 and summers or adders 134. The amplifiers 133 are weighted as indicated by the weighting coefficients $\omega 0$, $\omega 1$ and $\omega 2$. The weighting is not adaptive as with the delay units shown in FIG. 5. By way of example in the fourth order filter, a total of 17 coefficients can be provided in the filter network shown in FIG. 6. In the lattice type of realization shown the incoming signal is multiplied by the gain and added to the incoming signal with the signals going in the manner indicated by the arrows in FIG. 6. The resulting output 88 is designated as X1 for the first filter of the 13 band-pass filters. The selected output is supplied on the input line 88 to the air flow estimator 89.

After the band-pass filter has been selected which provides the maximum signal for the breathing noises emanating from the patient 22, the other band pass filters can be ignored and that same filter can be utilized in the sleep study throughout the evening. However if desired the algorithm can be such that after an appropriate period of time as for example five or ten minutes, another search can be conducted of the band pass filter network 87 to ascertain which band pass filter of the band pass filters 131 supplies the maximum output signal for the signal being received by the band pass filter network 87. Thus if the breathing pattern of the patient changes markedly, a different filter may be selected to achieve the maximum output to thereby provide an enhanced signal with a minimum noise content. The selected output 136 can be considered to be a third electrical signal and is connected to the line 88 connected to the air flow estimator 89.

Figure 7:
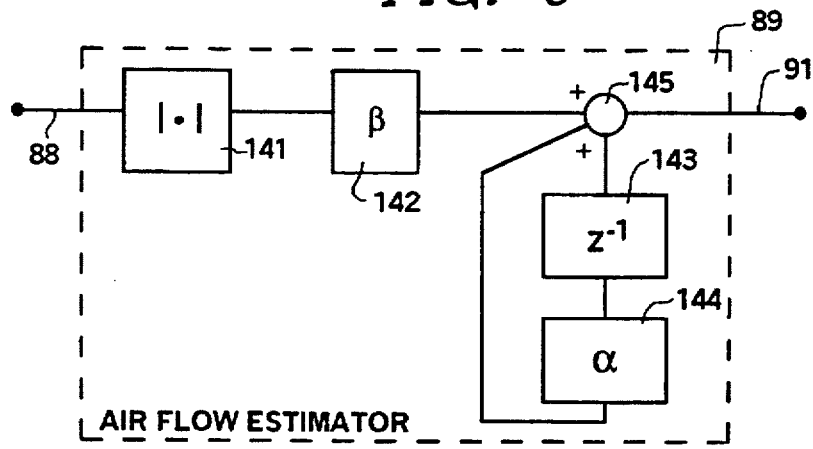
FIG. 7 is a more detailed block diagram of the air flow estimator shown in FIG. 4.

The air flow estimator 89 which is shown in FIG. 7 is used to determine the amount of air volume inhaled and exhaled by the patient in order to determine if the patient breathing is disordered. In order to generate an electrical waveform that is closely correlated with the air flow from the patient, the clean sound third electrical signal supplied on the line 88 is subjected to a process where it has been converted to fourth electrical signal representing a new waveform that correlates closely with air flow of the patient 22. This conversion process is performed digitally by an adaptive algorithm in the discrete-time domain and is somewhat similar to high order integration in the continuous time-domain. These new waveforms are obtained empirically by comparing them to results achieved from a standard polysomnogram (PSG). It has been found that transformation of the third electrical signal to a fourth electrical signal the air flow waveform correlates well with PSG air flow waveform.

The air flow estimation achieved by the air flow estimator 89 can be explained as follows. Let $\delta(n)$ be the estimate of the air flow at the time instant n. Then the estimated value air flow $\delta(n)$ can be given as:

$$\delta(n)=\alpha_1\Delta(n-1)+\alpha_2\delta(n-2)+\ldots+\alpha_k\Delta(n-k)+\beta|X(n)|$$

where $\alpha_i$ and $\beta$ coefficients are selected properly to make the system stable, i.e., $|\alpha_i|<1$ and $X(n)$ is the current microphones input signal.

If the implementation is in the digital Z domain the formula can be expressed as follows:

$$\frac{E(Z)}{X(Z)} = \beta \frac{Z^{k-1}}{(Z-\alpha_1)(Z-\alpha_2)\ldots(Z-\alpha_k)}$$

The continuous time equivalent of the system is an $n^{th}$ order integrator. The function of the air flow estimator 89 is shown in the block diagram in FIG. 7 in which the block 141 represents the absolute value which is computed in the manner hereinbefore described and is multiplied by $\beta$ as shown in the $\beta$ block 142, the output of which is supplied to a circle summer 143. The $Z^{-1}$ block 143 and the $\sigma$ block 144 which are serially connected and have their output connected back into the circular summer 145 represent the recursive nature of the time domain equation set forth above. It can be translated into a continuous time equation and its representation would be a plurality integrators.

Figure 8:
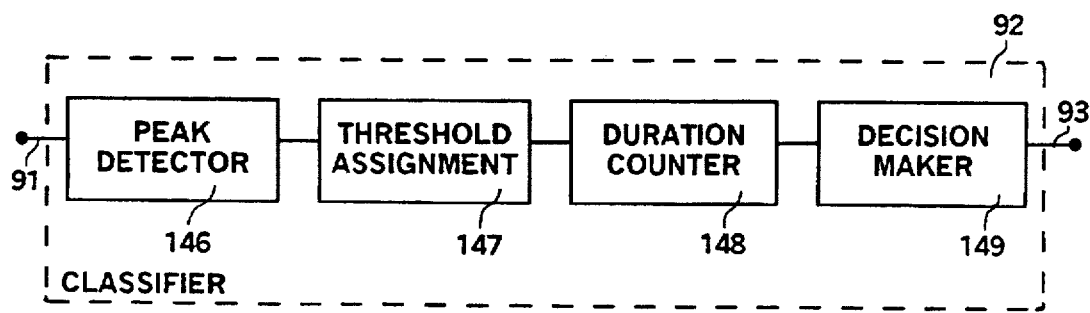
FIG. 8 is a more detailed block diagram of the classifier shown in FIG. 4.

The fourth electrical output 91 from the air flow estimator 89 representing the air flow of the patient is supplied to the classifier 92 shown in FIG. 8. The classifier 92 as shown in the block diagram FIG. 8 is comprised of a peak detector 146. Since the new waveform generated by the air flow estimator 89 correlates closely with actual patient air flow, the classifier 92 can make accurate decisions regarding the occurrence of disordered breathing events of the patient. For classification purposes, a time-varying nominal value is first assigned for the peaks by detecting the peaks of the waveform. These peaks are detected by the peak detector 146. Based on this value a threshold assignment is made as indicated by the block 147 is selected. This threshold value is selected as a certain percentage of the nominal values of the peaks as for example 50% of the nominal value. In the case of apnea, the peak value may be almost zero. In the case of hypopnea, the peak value is one which is typically reduced by 50% from the normal peak level. The cessation of air flow from the patient for a period of time greater than a predetermined period of time as for example a period of 10 seconds or more is ascertained by the decision counter 148.

Thus a peak value of from zero to 50% defines disordered breathing. The duration of this disordered breathing event is determined by the duration counter 148. Let it be assumed that the duration counter 148 has been set to produce an output signal when a disordered breathing event extends over a predetermined period of time as for example a period greater than 10 seconds but less than 100 seconds. An electrical signal is supplied to the decision maker 149 which produces a signal on line 93 when a disordered breathing event occurs. This is recorded as a disordered event in breathing in the LCD device 98 and which also provides a running total of the number of the disordered breathing events occurring during the sleep study of the patient. The function of each one of the blocks 146, 147, 148 and 149 can be implemented in software incorporated into the DSP chip in the control console 36.

Using a predetermined time interval of 10 seconds, if a disordered breathing event extends over a period of less than 10 seconds, it will not be scored by the control console 36. Similarly if the disordered breathing event extends over a period of greater than 10 seconds and up to a period of for example of 99 seconds it will be scored as a single disordered breathing event. This longer time period is utilized in the event the patient wakes up and goes to the bathroom.

It should be appreciated that the threshold assignment value can be readily adjusted in the control console. Thus for example a doctor administering the screening could set his own threshold to thereby determine the character of the disordered breathing event that should be recorded. In addition to adjusting the threshold, the doctor also could adjust the time duration for the duration counter 148.

Figure 9:
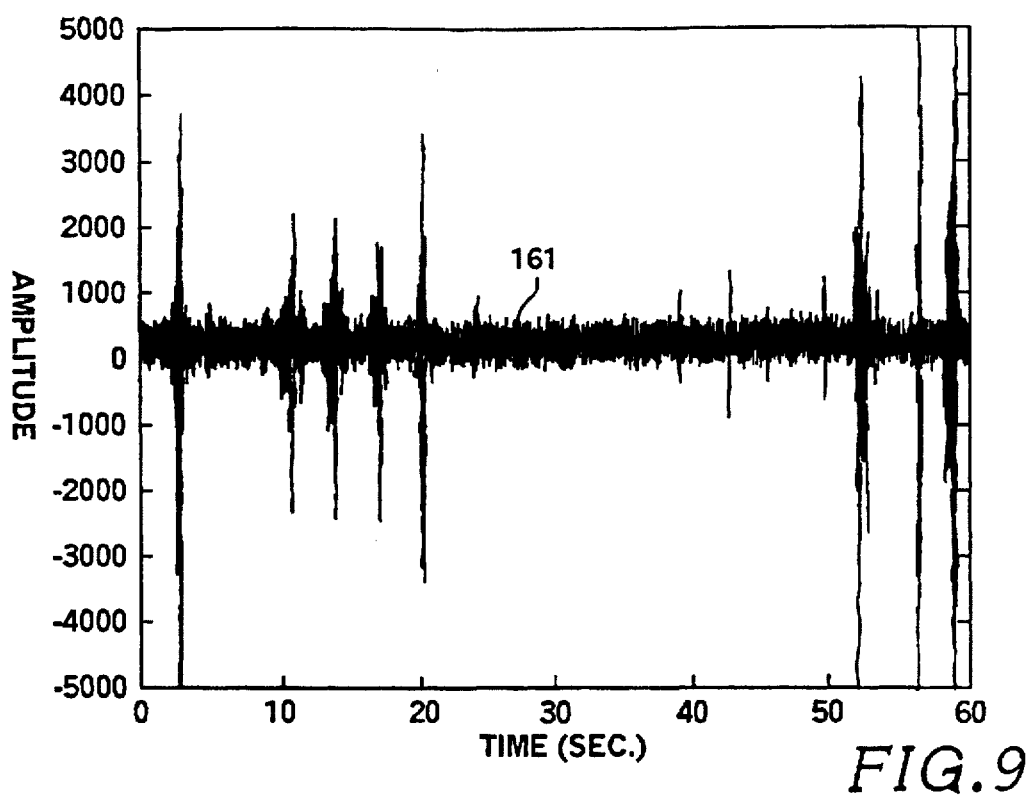
FIG. 9 is a graph showing a time domain sound waveform in raw form as it is picked up by an input microphone of the apparatus of the present invention and prior to processing of the waveform in accordance with the present invention.
Figure 10:
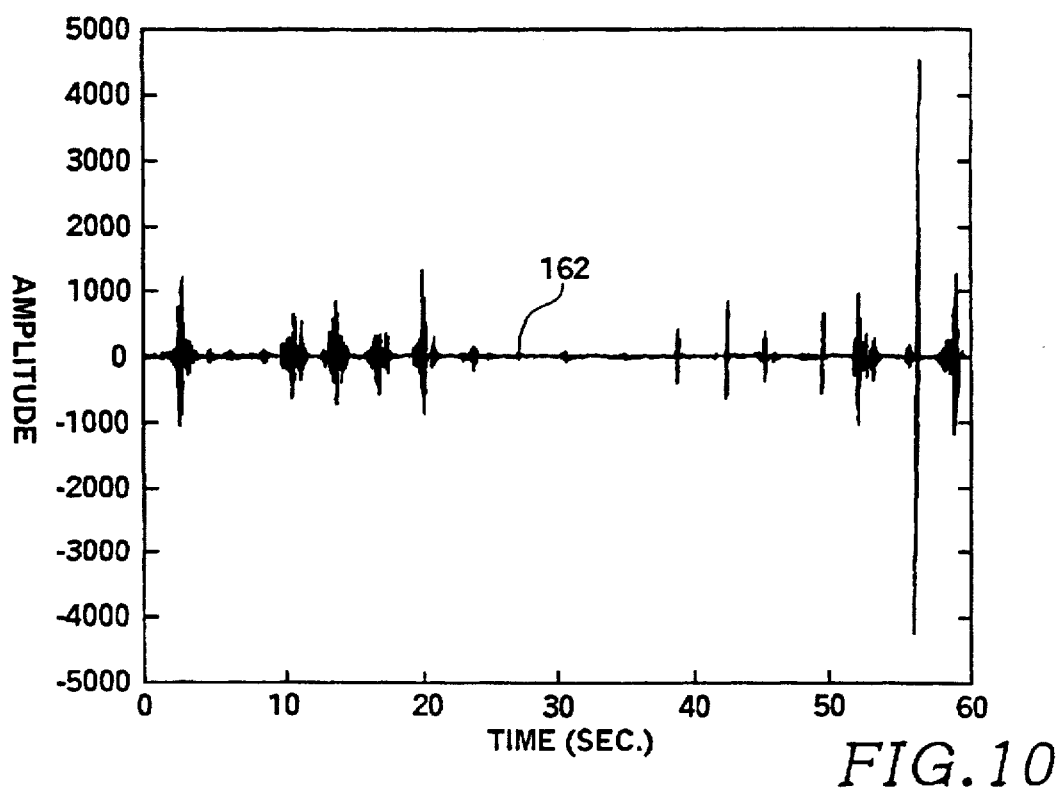
FIG. 10 is a graph showing the same waveform shown in FIG. 9 in the time domain after it has been processed by cleaning and band-pass filtering and just prior to air flow estimation.
Figure 11:
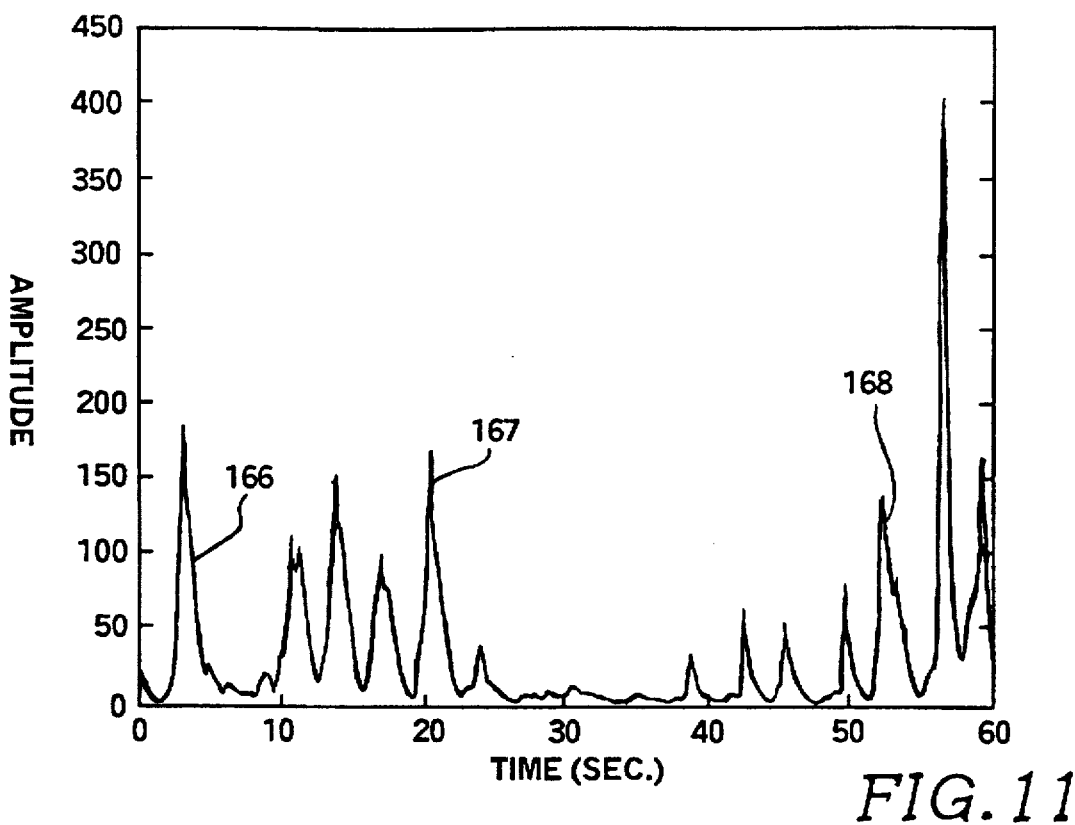
FIG. 11 is a graph showing the waveform in FIG. 10 after it has passed through the air flow estimator of the present invention and showing the occurrence of an hypopnea event.

The operation and use of the apparatus 21 to provide continuous monitoring for risk assessment of obstructive sleep apnea in performing the method of the present invention may now be briefly described as follows in conjunction with the waveforms which are shown in FIGS. 9 through 14. In FIG. 9, there is shown a waveform 161 which represents the raw electrical signal before any processing representing the acoustical sounds picked up by the sensing microphone 37. As shown, the electrical signal being produced is a very noisy signal but since the patient 22 is snoring loudly, the visual information representing such snoring is not lost in the noise. The graph in FIG. 10 shows a waveform 162 which is a cleaned and filtered version of the waveform 161 shown in FIG. 9 and is the signal appearing on the line 88 at the output from the band-pass filter network 87. The waveform 162 is visually informative and shows numerous peaks. This waveform 162 is supplied to the air flow estimator 89 which provides a waveform 166 which shows the occurrence of a hypopnea event in which the air flow for a period of time in excess of 10 seconds is 50% or less of the nominal peak level of breathing of the patient 22. This nominal peak level is represented by the spikes 167 and 168 between which the air flow is reduced to 50% or less for a period in excess of 10 seconds as for example the 30 seconds as shown. Such a hypopnea event would be recorded on the liquid crystal display 98.

Figure 12:
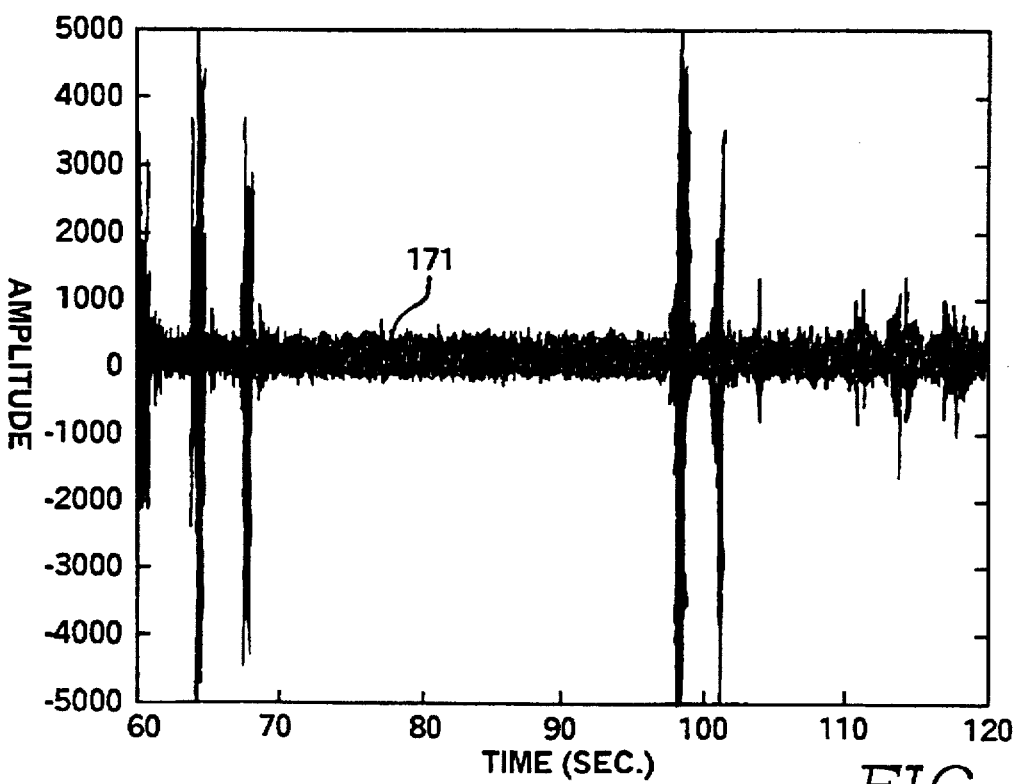
FIGS. 12, 13 and 14 show graphs which are similar to FIGS. 9, 10 and 11 and showing the occurrence of an apnea event.
Figure 13:
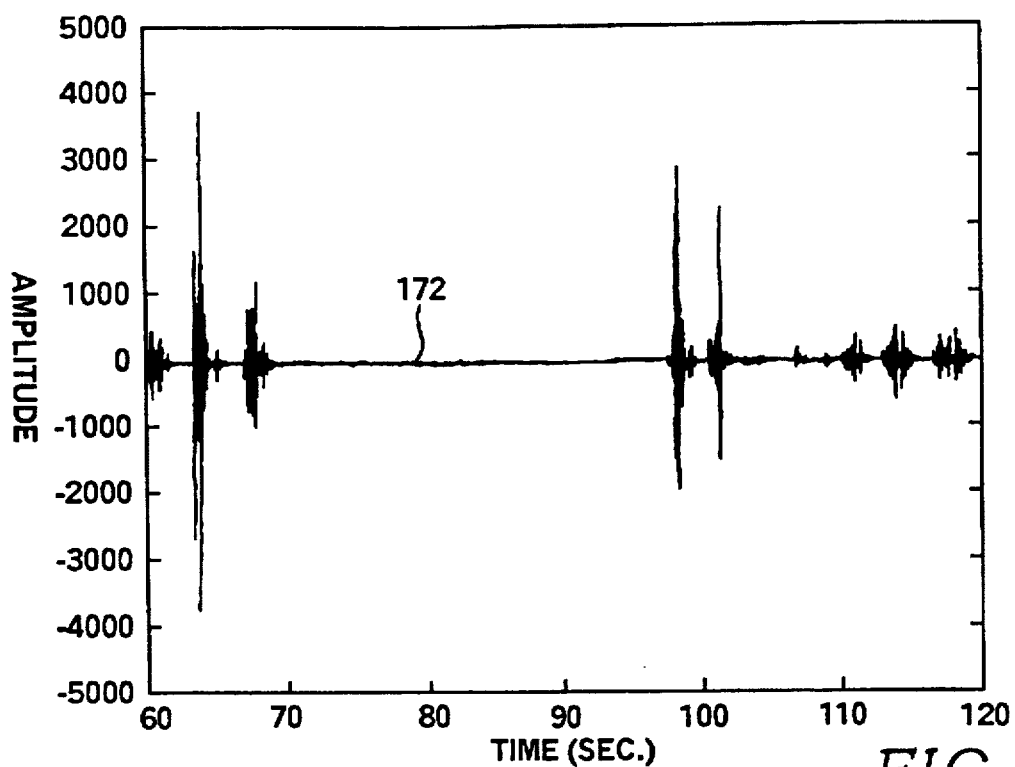
Figure 14:
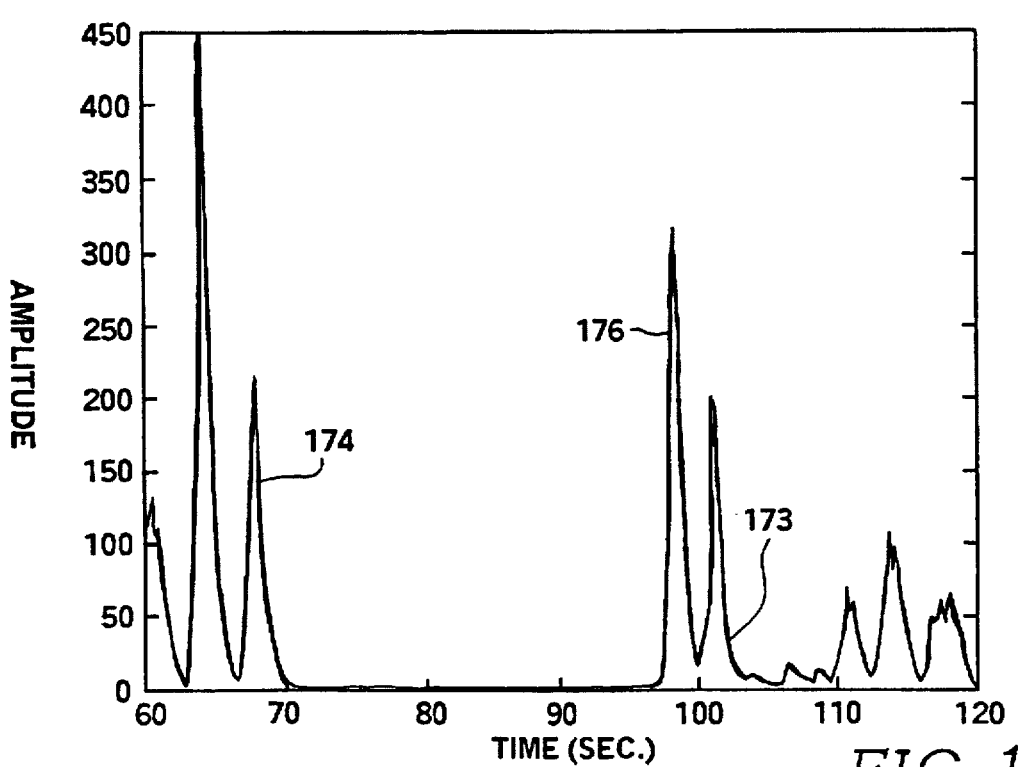

The waveform representing the recording of an apnea event is shown in FIG. 12, 13 and 14. FIG. 12 shows a waveform 171 representing the raw electrical output signal from the signal microphone 37 and as in the previous waveform 161 is a noisy waveform. In FIG. 13, thee is shown a waveform 172 representing the waveform 171 after it has been cleaned and filtered in the manner hereinbefore described. After passing through the air flow estimator 89, a waveform 173 is produced in which there is a substantial cessation of breathing for a period of approximately 30 seconds between peaks 174 and 176. In fact, which there is substantially no breathing activity during this period and thus utilizing the parameters hereinbefore described as an apnea event has occurred and would be so classified by the classifier 92 and counted by the event counter 94 with a signal being supplied to the liquid crystal display 98.

In this manner it can be seen that the apparatus of the present invention can be utilized to record breathing disorder events. The patient and/or the doctor observing the control console 36 can ascertain whether or not a disordered breathing event has taken place by the observation of the liquid crystal display 61. If desired, the patient can record the number of sleep disorder events over several nights if desired. The patient can then take the apparatus to the doctor's office with the number of sleep disorder events recorded thereon. It can be seen that the apparatus 21 makes it possible to provide a low cost easy-to-use and interpret portable ambulatory risk assessment device with continuous monitoring capabilities that can handle data with a high degree of accuracy. The apparatus is technically based on sensing respiratory sounds, (breathing/snoring). Patients with sleep related breathing disorders using the device of the present invention can be screened by the doctor before they are subjected to further sleep laboratory investigations. In addition, patients can be monitored on a continuous basis after they undergo surgery or during therapy or a treatment evaluation period. With the apparatus of the present invention, disordered breathing events recorded and each event is logged cumulatively in real time on the liquid crystal display.

What is claimed:

1. A sleep apnea screening and/or detection apparatus for use by a patient having lungs and a nose and mouth in communication with the lungs and breathing through the nose and/or mouth and producing an air flow into and out of the lungs and creating audible sounds comprising a first microphone adapted to be positioned adjacent the patient's nose and/or mouth to pick up directly audible breathing sounds created by breathing of the patient and providing a first electrical analog signal, a second microphone adapted to be positioned near the patient but spaced from the first microphone and out of contact with the patient for picking up ambient audible noise in the vicinity of the patient and providing a second electrical analog signal, means operating on and combining the first and second electrical analog signals to provide a third electrical signal, means operating on the third electrical signal for generating a fourth electrical signal providing a waveform which is closely correlated with the air flow of the patient and electrical classifier means for classifying the electrical waveform provided by the fourth electrical signal to determine when a disordered breathing event has occurred.

2. A sleep apnea screening and/or detection apparatus for use by a patient having lungs and a nose and mouth in communication with the lungs and breathing through the nose and/or mouth and producing an air flow into and out of the lungs and creating audible sounds comprising a first microphone adapted to be positioned adjacent the patient's nose and mouth and out of contact therewith to pick up audible sounds created by breathing of the patient and providing a first electrical analog signal, a second microphone adapted to be positioned near the patient for picking up ambient noise in the vicinity of the patient and providing a second electrical analog signal, means operating on and combining the first and second electrical analog signals to provide a third electrical signal, means operating on the third electrical signal for generating a fourth electrical signal providing a waveform which is closely correlated with the air flow of the patient and electrical classifier means for classifying the electrical waveform provided by the fourth electrical signal to determine when a disordered breathing event has occurred, said means operating on the third electrical signal including means for converting the third electrical signal to positive absolute values and sequentially integrating the positive absolute values of the third electrical signal with adjusted time constants to provide the fourth electrical signal.

3. Apparatus in claim 2 wherein said means for operating on the third electrical signal utilizes the formula $$\delta(n)=\alpha_1\Delta(n-1)+\alpha_2\delta(n-2)+ \ldots +\alpha\Delta(n-k)+\beta|X(n)|$$

where $\alpha$ and $\beta$ are selected coefficients.

4. Apparatus in claim 1 wherein said electrical classifier means includes a peak detector for ascertaining a nominal peak value for the peaks in the waveform of the fourth electrical signal, a threshold detector having a predetermined threshold value which is a percentage of the nominal peak value for ascertaining when the fourth electrical signal reaches said predetermined value, time duration counting means for measuring elapsed time connected to the threshold detector for ascertaining the time which elapsed after the threshold detector detects a value which is less than the predetermined value and decision making means for ascertaining when the predetermined threshold has not been reached for a predetermined period of elapsed time to establish that a disordered breathing event has occurred.

5. A sleep apnea screening and/or detection apparatus for use by a patient having lungs and a nose and mouth in communication with the lungs and breathing through the nose and/or mouth and producing an air flow into and out of the lungs and creating audible sounds comprising a first microphone adapted to be positioned adjacent the patient's nose and mouth and out of contact therewith to pick up audible sounds created by breathing of the patient and providing a first electrical analog signal, a second microphone adapted to be positioned near the patient for picking up ambient noise in the vicinity of the patient and providing a second electrical analog signal, means operating on and combining the first and second electrical analog signals to provide a third electrical signal, means operating on the third electrical signal for generating a fourth electrical signal providing a waveform which is closely correlated with the air flow of the patient and electrical classifier means for classifying the electrical waveform provided by the fourth electrical signal to determine when a disordered breathing event has occurred, an analog-to-digital converter for receiving the first electrical analog signal and converting it to a first electrical digital signal, adaptive filter means for receiving the first electrical digital signal and selectively tapping the first electrical digital signal to provide a first electrical digital signal which is delayed in time, an analog-to-digital converter for converting the second electrical analog signal to a second electrical digital signal and delay means for delaying the second electrical digital signal so that the time-delay corresponds to the time-delay provided by the adaptive filter so that the first electrical digital signal and the second electrical signal are supplied substantially in unison in time to the means for combining the first and second electrical analog signals.

6. Apparatus as in claim 1 further including a band-pass filter network for filtering the third electrical signal.

7. Apparatus in claim 5 wherein said band-pass filter network includes a plurality of band pass filters and means for selecting which of the plurality of band pass filters provides the greatest output.

8. Apparatus in claim 5 wherein said adaptive filter means includes a Motorola DSP56002 chip and in which the sampling frequency is 5.6 kilohertz and a range of taps from 50 to 200 is selected.

9. Apparatus as in claim 5 wherein the band-pass filter network has a spectrum of 200 Hz to 1500 Hz and wherein each band-pass filter has a band-pass of approximately 100 Hz.

10. Apparatus as in claim 1 together with display means for displaying in real time the occurrence of a disordered breathing event of the patient.

11. Apparatus as in claim 9 wherein the display means includes means for cumulating in real terms all disordered breathing events of the patient over a predetermined period of time.

12. A method for screening and/or detection of sleep apnea in a patient having lungs and a nose and mouth in communication with the lungs and breathing through the nose and/or mouth and producing an air flow into and out of the lungs and creating audible sounds comprising detecting directly audible breathing sounds created at the patient's mouth and/or nose and providing a first electrical analog signal in response thereto, detecting audible sounds in a space remote from the patient's nose and mouth which represent ambient noise to provide a second analog electrical signal, operating on the first and second electrical analog signals and combining the first and second electrical analog signals to provide a third electrical digital signal in which unwanted ambient noise is reduced, utilizing the third electrical digital signal to generate a fourth electrical signal providing an electrical waveform that closely approximates the air flow of the patient and classifying the electrical waveform to determine when a disordered breathing event has occurred.

13. A method for screening and/or detection of sleep apnea in a patient having lungs and a nose and mouth in communication with the lungs and breathing through the nose and/or mouth and producing an air flow into and out of the lungs and creating audible sounds comprising detecting directly audible sounds in the vicinity of the patient's mouth and/or nose and providing a first electrical analog signal in response thereto, detecting audible sounds in a remote space from the patient's nose and mouth which represent ambient noise to provide a second analog electrical signal, operating on the first and second electrical analog signals and combining the first and second electrical analog signals to provide a third electrical digital signal in which unwanted ambient noise is reduced, utilizing the third electrical digital signal to generate a fourth electrical signal providing an electrical waveform that closely approximates the air flow of the patient and classifying the electrical waveform to determine when a disordered breathing event has occurred, the step of generating the fourth electrical signal to provide the electrical waveform being accomplished by sequentially integrating the third electrical signal with adjustable time constants.

14. A method as in claim 13 wherein the waveform is generated by converting the third electrical signal to positive absolute values and sequentially integrating the positive absolute values of the third electrical signal with adjusted time constants to provide the fourth electrical signal.

15. A method as in claim 12 wherein the step of classifying the electrical waveform includes ascertaining a nominal value for the peaks in the electrical waveform, detecting when the peaks in the electrical waveform are less than a predetermined percentage of the nominal value of peaks and ascertaining when the elapsed time during which a peak does not exceed a predetermined threshold to determine when a disordered breathing event has occurred.

16. A method as in claim 12 further comprising the step of counting in real time each disordered breathing event.

17. A method for screening and/or detection of sleep apnea in a patient having lungs and a nose and mouth in communication with the lungs and breathing through the nose and/or mouth and producing an air flow into and out of the lungs and creating audible sounds comprising detecting directly audible sounds in the vicinity of the patient's mouth and/or nose and providing a first electrical analog signal in response thereto, detecting audible sounds in a remote space from the patient's nose and mouth which represent ambient noise to provide a second analog electrical signal, operating on the first and second electrical analog signals and combining the first and second electrical analog signals to provide a third electrical digital signal in which unwanted ambient noise is reduced, utilizing the third electrical digital signal to generate a fourth electrical signal providing an electrical waveform that closely approximates the air flow of the patient and classifying the electrical waveform to determine when a disordered breathing event has occurred, further comprising the step of converting the first electrical analog signal to a digital signal and adaptively filtering the digital signal, converting the second electrical analog signal to a digital signal, delaying the second electrical signal so that the digital signal from the first electrical signal and the digital signal from the second electrical signal are combined at the same time to provide the third electrical signal.

18. A method as in claim 17 further comprising the step of filtering the third electrical signal in successive band passes to select a band through which the third electrical signal passes with a maximum output.

* * * * *